United States Patent
Giessler-Blank et al.

(10) Patent No.: US 8,163,673 B2
(45) Date of Patent: Apr. 24, 2012

(54) NON-FOAMING ORGANIC SURFACTANTS AS ADDITIVES FOR TANK MIXTURE PREPARATIONS IN CROP PROTECTION

(75) Inventors: Sabine Giessler-Blank, Dortmund (DE); Ewald Sieverding, St. Johann (DE); Ingo Fleute-Schlachter, Essen (DE)

(73) Assignee: Evonik Goldschmidt GmbH, Essen (DE)

(*) Notice: Subject to any disclaimer, the term of this patent is extended or adjusted under 35 U.S.C. 154(b) by 83 days.

(21) Appl. No.: 12/605,630

(22) Filed: Oct. 26, 2009

(65) Prior Publication Data

US 2010/0105555 A1 Apr. 29, 2010

(30) Foreign Application Priority Data

Oct. 27, 2008 (DE) .......................... 10 2008 043 185

(51) Int. Cl.
- *A01N 25/02* (2006.01)
- *A01N 25/00* (2006.01)
- *C07D 4/00* (2006.01)

(52) U.S. Cl. ...................... 504/362; 504/116.1; 106/285
(58) Field of Classification Search ................... 504/362, 504/116.1; 106/285
See application file for complete search history.

(56) References Cited

U.S. PATENT DOCUMENTS 5,223,177 A * 6/1993 Topfl et al. .................... 516/134

FOREIGN PATENT DOCUMENTS

| EP | 0 791 384 | 8/1997 |
| EP | 1 314 356 | 5/2003 |
| JP | 2002 128603 | 5/2002 |
| WO | WO 98/35553 | 8/1998 |
| WO | WO 2008/024308 | 2/2008 |
| WO | WO 2008/037374 | 4/2008 |

* cited by examiner

*Primary Examiner* — Johann Richter
*Assistant Examiner* — Jane C Osweicki
(74) *Attorney, Agent, or Firm* — Frommer Lawrence & Haug LLP

(57) ABSTRACT

Use of special non-foaming alkoxylated alcohols alone or their mixture with polysiloxanes as tank mixture additive for crop protection composition formulations.

5 Claims, No Drawings

NON-FOAMING ORGANIC SURFACTANTS AS ADDITIVES FOR TANK MIXTURE PREPARATIONS IN CROP PROTECTION

This application claims benefit under 35 U.S.C. 119(a) of German patent application DE 102008043185.0, filed on Oct. 27, 2008.

Any foregoing applications including German patent application DE 10 2008 043 185.2, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to the use of additives in preparations of crop protection composition spray mixtures, in particular as additives for tank mixtures to pesticides, pesticide mixtures or crop protection compositions in general. In crop protection, additives, also called adjuvants or auxiliaries below, are usually used to improve the efficiency and the effectiveness of crop protection composition active ingredients. These are either added to the aqueous spray mixture shortly before spraying separately from the crop protection composition (as tank mixture additive) or incorporated directly into the crop protection composition concentrate together with other auxiliaries (formulation). Chemical or biological crop protection compositions (also called pesticides below) or pesticide mixtures are used. These may be, for example, herbicides, fungicides, insecticides, growth regulators, molluscicides, bactericides, viricidal micronutrients and also biological crop protection compositions based on natural substances or living or manufactured or cultivated microorganisms. Pesticidal active ingredients are listed in connection with their fields of use e.g. in "The Pesticide Manual", 14th edition, 2006, The British Crop Protection Council; biological active ingredients are given, for example, in "*The Manual of Biocontrol Agents*", 2001, The British Crop Protection Council.

The tank mixture additives used are often alkoxylated trisiloxane surfactants which reduce the static surface tension of spray mixtures or water to a significantly greater extent than organic surfactants. These trisiloxane surfactants have the structure $Me_3O$—SiMeR—$OSiMe_3$, where the radical R is a polyether radical. The use of these super-spreading trisiloxane surfactants, such as, for example, BREAK-THRU® S-240, Evonik Goldschmidt GmbH, in combination with a pesticide leads to an improvement in the pesticide uptake by the plant and generally to an increase in its effectiveness or its efficiency. U.S. Pat. No. 6,734,141 describes that especially a low surface tension and not necessarily the spreading is responsible for this increase in efficiency. In most patents, the term surface tension is always understood as meaning the static surface tension. For increased retention of the active ingredient on the leaf, however, the dynamic surface tension, which is measured at a bubble residence time of ca. 30 ms, is decisive. The static surface tension, by contrast, is measured at ca. 5000 ms. The surface tension of the spray mixtures is based here on the measurement by means of a bubble pressure tensiometer (Sita online t 60). For trisiloxanes, the dynamic surface tension is about 60 mN/m, whereas the static surface tension is ca. 21 mN/m.

In view of an increase in environmental awareness, some synthetic (e.g. TAEs, NPEs) surfactants have increasingly become the subject of criticism in recent years on account of their low biodegradability. This is specifically valid for surfactants which are classified as harmful to health. A further disadvantage of many tank mixture additives, specifically of alkoxylated products is that they cause spray mixtures to foam greatly as they are stirred in.

The specialist literature discloses organic surfactants which do not lead to the disadvantages mentioned above. In most cases, however, these are used as additives for active ingredient concentrates and concentrated compositions and specifically as dispersants. Thus, EP 1 313 792 (U.S. Pat. No. 6,884,286) indicates compounds with at least 3 ethylene oxide units and 4 propylene oxide units whose static surface tension is greater than 30 mN/m. EP 0 959 681 (U.S. Pat. No. 6,413,908) describes aqueous agrochemical compositions with alkoxylated primary and secondary alcohols which have static surface tensions of more than 30 mN/m.

JP 2002-128603 describes exclusively ethoxylated spreaders with a static surface tension of 30-45 mN/m, which have a strong tendency towards foaming.

Further wetting agents which are widespread in the agricultural sector, such as, for example, nonylphenol ethoxylates (NPE) or tallow amine ethoxylates (TAE), have for a long time been the subject of discussion on account of their poor toxicity and have already been banned as pesticide additive in numerous countries. NPEs are used primarily as surfactants and emulsifiers. Biodegradation forms nonylphenols (NP), which can only be degraded with difficulty. They pass via industrial and communal effluent into waters. On account of their characterization of causing irreversible eye damage, TAEs are the subject of discussion. They likewise lead to skin irritations and the fish and algae toxicities have values of less than 1. The acute oral toxicity in rats is below the value of 4000 mg/kg, which is respected for green labels, namely only 200-2000 mg/kg.

Crop protection composition formulations which are products which are in most cases diluted with water for their application prior to customary spraying via nozzles contain, besides the effective component (active substance or also called active ingredient), also other auxiliaries, such as emulsifiers, dispersion auxiliaries, antifreezes, antifoams, biocides and surface-active substances; such substances are known to the person skilled in the art of formulation.

Such crop protection compositions are often added to a tank with water as ingredient in order to dilute the concentrated formulation and make it compatible with the plants prior to spraying. Tank mixture additives (also called adjuvants) are added to the water in the same tank separately before or after the crop protection composition formulation and are distributed with the entire spray mixture by stirring.

Active substances are those which are approved and/or registered and/or listed in the individual countries for use for planting and cultivation in order to protect plants against damage, or in order to avoid the yield loss during a cultivation. Such active substances or active ingredients may be synthetic in nature, or else biological in nature. Such active ingredients may also be extracts, or natural substances, or antagonistically active organisms. They are usually also referred to as pesticides. In this invention present here, the type of active ingredient is irrelevant since the use as tank mixture additive is general in nature and is not specifically related to the active ingredient. The pesticides which are named according to their field of use in crop protection include the following classes: all acaricides (AC), algicides (AL), attractants (AT), repellents (RE), bactericides (BA), fungicides (FU), herbicides (HE), insecticides (IN), agents to combat snails and slugs (molluscicides, MO), nematicides (NE), rodenticides (RO), sterilants (ST), viricides (VI), growth regulators (PG), plant strengthening agents (PS), micronutrients (MI) and macronutrients (MA). These designations and the fields of application are known to the person skilled in the art. Active ingredients are used alone or in combinations with other active ingredients. Preferred pesticides are HB, FU, IN, PG, MI and particularly HB, FU, IN.

Some active ingredients or active organisms are listed, for example, in "The Pesticide Manual", 14th edition, 2006, The British Crop Protection Council, or in "The Manual of Biocontrol Agents", 2004, The British Crop Protection Council. The present application, however, is not limited to these active ingredients listed therein, but also includes more modern active ingredients not yet cited in the aforementioned monograph.

The group of herbicides includes, by way of example but not limited to these, products with the following active ingredients or active ingredient mixtures: acetochlor, acifluorfen, aclonifen, acrolein, alachlor, ametryne, amitrole, asulam, atrazine, benazolin, bensulfuronmethyl, bentazon, benzofenap, bialaphos, bifenox, bromacil, bromobutide, bromofenoxim, bromoxynil, butachlor, butafenacil, chlomethoxyfen, chloramben, chloroacetic acid, chlorbromuron, chlorimuron-ethyl, chlorotoluron, chlomitrofen, chlorotoluron, chlorthaldimethyl, clomazone, clodinafop, clopyralid, clomeprop, cyanazine, 2,4-D, 2,4-DB, dimuron, dalapon, desmedipham, desmetryn, dicamba, dichlobenil, dichloroprop, diclofop, difenzoquat, diflufenican, dimefuron, dimethachlor, dimethametryn, dimethenamid, dinitramine, diquat, diuron, endothall, ethametsulphuron-methyl, ethofumesan, fenac, fenclorim, fenoxaprop, fenoxaprop-ethyl, flampropmethyl, flazasulfuron, fluazifop, fluazifop-p-butyl, flumetsulam, flumiclorac-penyl, fluoroglycofen, flumetsulam, flumeturon, flumioxazin, flupoxam, flupyrsulfuron, flupropanate, fluridone, fluoroxypyr, flurtamone, fomasafen, fosamine, glufosinate, glyphosate and its salts, (for example alkylammonium or alkali metal salts), haloxyfop, imazameth, imazamethabenz, imazamox, imazapic, imazapyr, imazaquin, imazethapyr, iodosulfuron, ioxynil, isoproturon, isoxaben, isoxapyrifop, lactofen, lenacil, linuron, MCPA, MCPB, mecoprop, mefenacet, mesotrione, metazachlor, methabenzthiazuron, metalachlor, methylarsenic acid, metolachlor, metobromuron, metosulam, mesosulfuron, metamitron, metsulfuron, naproanilide, naptalam, neburon, nicosulfuron, nonanoic acid, norflurazon, oryzalin, oxadiazon, oxyfluorfen, paraquat, pendimethalin, phenmedipham, picloram, picolinafen, pretilachlor, prodiamine, prometon, prometryn, propachlor, propazine, propisochlor, propyzamide, pyrazolynate, pyrazosulfuron-ethyl, pyributicarb, pyridat, quinclorac, quizalofop-ethyl, quizalofop-P, quinclorac, rimsulfuron, siduron, simazine, simetryn, sulphamic acid, sulphonylurea, 2,3,6-TBA, terbumeton, terbuthylazine, terbutryn, trichloroacetic acid, triclopyr, trietazine, thenylchlor, thiazopyr, tralkoxydim, trifuralin, tritosulfuron, and salts thereof and mixtures thereof.

In another embodiment of the invention, the herbicides are aryloxyphenoxypropionic herbicides which includes chlorazifop, clodinafop, clofop, cyhalofop, diclofop, fenoxaprop, fenoxaprop-P, fenthiaprop, fluziafop, fluziafop-P, haloxyfop, haloxyfop-P, isoxapyrifop, metamifop, propaquizafop, quizalofop, quizalofop-P, trifop, and salts thereof and mixtures thereof.

Examples of active fungicide active ingredients which are combined in crop protection composition products alone or in a mixture with other active ingredients are: azoxystrobin, benalaxyl, benomyl, bitertanol, borax, bromocuonazole, sec-butylamine, captafol, captan, calcium polysulphide, carbendazim, quinomethionate, chlorothalonil, chlozolinate, copper and its derivatives, copper sulphate, cyprodinil, cyproconazole, dichlofluanid, dichlorophen, diclomezine, dicloran, diethofencarb, difenoconazole, dimethomorph, diniconazole, dithianon, epoxiconazole, famoxadone, fenarimol, fenbuconazole, fenfuram, fenhexamid, fenpiclonil, fenpropidin, fenpropimorph, fentin, fluazinam, fludioxonil, fluoroimide, fluquinconazole, flusulfamide, flutolanil, folpet, fosetyl, furalaxyl, guazatine, hexachlorobenzene, hexaconazole, hydroxyquinoline sulphate, imibenconazole, iminoctadine, ipconazole, iprodione, kasugamycin, kresoxim-methyl, mancozeb, maneb, mefenoxam, mepanipyrim, mepronil, mercury chloride, metam, metalaxyl, metconazole, metiram, nabam, nickel bis(dimethyldithiocarbamate), nuarimol, oxadixil, oxine-copper, oxolinic acid, penconazole, pencycuron, picoxystrobin, phthalide, polyoxin B, prochloraz, procymidone, propamocarb, propiconazole, propineb, pyrifenox, pyraclostrobin, pyroquilon, quintozene, spiroxamine, sulphur, tebuconazole, tecloftalam, tecnazene, thiabendazole, thifluzamide, thiophanate-methyl, thiram, tolclofos-methyl, tolylfluanid, triadimefon, triadimenol, triazoxide, trifloxystrobin, triforin, triticonazole, vinclozolin, zineb, ziram, salts thereof and mixtures thereof.

In another embodiment of the invention, the fungicides are strobilurin and related fungicides classes of chemistries which include azoxystrobin, enestrobin, picoxystrobin, pyraclostrobin, kresoxim-methyl, trifloxystrobin, dimoxystrobin, metominostrobin, orysastrobin, famoxadone, fluoxastrobin, fenamidone, pyribencarb, cyazofamid, amisulbrom, and mixtures thereof; these fungicides and mixtures thereof are used in cereals (wheat, barley, rye, triticale, rice) to control crop diseases.

Examples of active ingredients (alone or in mixtures) of insecticides are: abamectin, acephate, acetamiprid, acrinathrin, amitraz, azadirachtin, azamethiphos, azinphos-methyl, azocyclotin, bensultap, bifenthrin, bromopropylate, buprofezin, butoxycarboxim, cartap, chlorfenapyr, chlorfenson, chlorfluazuron, clofentezine, coumaphos, cyfluthrin, beta-cyfluthrin, lambda-cyhalothrin, cypermethrin, alpha-cypermethrin, theta-cypermethrin, cyromazine, DDT, deltamethrin, diafenthiuron, dicofol, dicrotophos, difenthiuron, diflubenzuron, dimethoate, emamectin benzoate, endosulfan, esfenvalerate, etoxazole, fenazaquin, fenbutatin oxide, fenoxycarb, fenpyroximate, fipronil, fluazuron, flucycloxuron, flufenoxuron, tau-fluvalinate, formetanate, furathiocarb, halofenozide, gamma-HCH, hexaflumuron, hexythiazox, hydramethylnon, hydrogen cyanide, imidacloprid, lufenuron, methamidophos, methidathion, methiocarb, methomyl, methoxychlor, mevinphos, milbemectin, mineral oils, monocrotophos, nicotin, nitenpyram, novaluron, omethoate, organophosphorus compounds, oxamyl, oxydemeton-methyl, pentachlorophenol, phosphamidon, pymetrozin, permethrin, profenofos, pyridaben, rapeseed oil, resmethrin, rotenone, spinosad, sulfluramid, tebufenozide, tebufenpyrad, tebupirimfos, teflubenzuron, tetrachlorvinphos, tetradifon, tetramethrin, thiamethoxam, thiocyclam, thiodicarb, tralomethrin, trichlorfon, friflumuron, trimethacarb, vamidothion, and salts thereof and mixtures thereof.

Examples of active ingredients in products from the group of growth regulators are: 6-benzylaminopurine, chlormequat, chlorphonium, cimectacarb, clofencet, cloxyfonac, cyanamide, cyclanilide, daminozide, dikegulac, ethephon, flumetralin, forchlorfenuron, gibberilic acid, inabenfide, indolylbutyronic acid, 2-(1-naphthyl)acetamide, mepiquat, paclobutrazol, N-phenyl-phthalaminic acid, thidiazuron, trinexapac-ethyluniconzole, and salts thereof and mixtures thereof. Products with natural substance character, or biological products are listed in the aforementioned specification. Plant nutrients and plant micronutrients which are applied in liquid form in liquid preparation in highly diverse forms alone or in combination with other nutrients or in combination with crop protection compositions are for example nitrogen, phosphate, potassium, calcium, magnesium, manganese, boron, copper, iron, selenium, cobalt, and others which are known under the name micronutrients.

There is therefore a need for substances which have a very low dynamic surface tension, do not foam much, are toxicologically acceptable, are water-soluble or dispersible and can be used as tank mixture additive at concentrations from 0.001 to 0.5% by volume, preferably 0.001 to 0.39% by volume and particularly preferably below 0.001 to 0.1% by volume (ca. correspondingly also 0.1% by weight) of the spray mixture. This is equivalent to 10 to 1000 ml/ha, and preferably an amount of from 50 to 500 ml/ha, which are added to the particular spray mixture amounts irrespective of the total water application rate per ha.

It was therefore an object of the present invention to provide alternative organic surfactants which are suitable for use as tank mixture additive in spray mixtures, are toxicologically acceptable, do not produce foam in spray mixtures and generate a significantly reduced dynamic surface tension in water than trisiloxane surfactants. This reduced dynamic surface tension should occur in particular at concentrations less than 0.1% by weight, equivalent to 0.1% by volume.

The non-expert will maybe assume that all commercial wetting agents or tensides (e.g. in cosmetic uses or as component of household cleaning compositions) will promote the efficiency of pesticides. This is wrong and has been shown in several publications e.g. in Pesticide Formulation and Adjuvant Technology, edited by Chester L. Foy and David W. Pritchard. CRC Press LLC, 1996, Seiten 323-349).

It is therefore still surprising and not apparent that the substances of the present invention can improve the efficiency of pesticides—that means they act as an adjuvant.

Within the context of the invention, numerous organic surfactants were tested; of these, surprisingly, specifically alkoxylated alcohols proved to be suitable. In this connection, the starting alcohol for the preparation of the alkoxylated alcohol proved to be a decisive feature besides the degree of alkoxylation.

The structure of the substance on which the invention is based for achieving the objective can be described as follows: Alkoxylated Alcohols of the Formula $$R^1O(SO)_a(PO)_b(EO)_c(BO)_dR^2 \quad \text{(Formula 1)}$$

where
SO=styryloxy=—CH(C$_6$H$_5$)—CH$_2$—O— or —CH$_2$—CH(C$_6$H$_5$)—O—,
PO=propyleneoxy=—CH(CH$_3$)—CH$_2$—O— or —CH$_2$—CH(CH$_3$)—O—,
EO=ethyleneoxy=—CH$_2$—CH$_2$—O—,
BO=butyleneoxy=—CH$_2$—CH$_2$—CH$_2$—CH$_2$—O—,
a=0 to 1, preferably 0,
b=0.5 to 4, preferably 2 to 3, in particular 3,
c=1 to 5, preferably 2 to 4.5, but in particular 3 to 4 and
d=0 to 1, preferably 0 and
R$^1$ is a branched alkyl radical having 6 to 22 carbon atoms or is a mixture of such alkyl radicals, but is specifically a 3,5,5-trimethylhexyl radical and
R$^2$ is an alkyl radical having 1 to 4 carbon atoms, an acyl radical, or a (meth)acryloxy radical, or is a hydrogen radical, preferably a methyl radical or hydrogen radical.

It is preferred here for the EO in the block to be terminal, it also being possible for the PO block to be terminal.

In the structure according to the invention, the dynamic surface tension for a bubble residence time of 30 ms in 0.1% strength by weight aqueous solution is less than 35.3 mN/m, and the static surface tension for a bubble residence time of 5000 ms is less than 28 mN/m.

Mixtures of compounds according to Formula 1 and polysiloxanes of general Formula 2 have also proven to be furthermore advantageous.

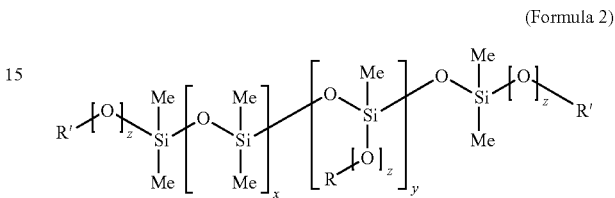

(Formula 2)

where
z=0 or 1,
x=0 to 100,
y=preferably greater than or equal to 0,
R'=R or an alkyl radical having 1 to 8 carbon atoms or a hydrogen atom,
R=C$_n$H$_{2n}$O(C$_e$H$_{2e}$O)$_p$K,
n=3 to 4,
e=identical or different 2 to 4,
p=greater than or equal to 3,
K=H, an alkyl radical having 4 or fewer carbon atoms.

The mixing of the components of Formulae 1 and 2 is here in the ratio 90:10 to 10:90, but particularly 80:20 to 50:50.

Thus, the compounds according to the invention corresponding to Formula 1 can achieve, alone and also their mixture with a polysiloxane of Formula 2 at use concentrations of from 0.001 to 0.5% by volume, preferably from 0.001 to 0.39% by volume, in water and particularly preferably from 0.05 to 0.15% by volume (corresponding also to % by weight), low dynamic and low static surface tensions without foam appearing.

This corresponds to an active ingredient concentration of from 10 to 1000 ml/ha in the spray mixture.

The invention therefore provides the use of alkoxylated alcohols of the formula $$R^1O(SO)_a(PO)_b(EO)_c(BO)_dR^2 \quad \text{(Formula 1)}$$

where
SO=styryloxy=—CH(C$_6$H$_5$)—CH$_2$—O— or —CH$_2$—CH(C$_6$H$_5$)—O—,
PO=propyleneoxy=—CH(CH$_3$)—CH$_2$—O— or —CH$_2$—CH(CH$_3$)—O—,
EO=ethyleneoxy=—CH$_2$—CH$_2$—O—,
BO=butyleneoxy=—CH$_2$—CH$_2$—CH$_2$—CH$_2$—O—,
a=0 to 1, preferably 0,
b=0.5 to 4, preferably 2 to 3, in particular 3,
c=1 to 5, preferably 2 to 4.5, in particular 3 to 4 and
d=0 to 1, preferably 0 and
R$^1$ is a branched alkyl radical having 6 to 22 carbon atoms or is a mixture of such alkyl radicals, preferably a 3,5,5-trimethylhexyl radical and
R$^2$ is an alkyl radical having 1 to 4 carbon atoms, an acyl radical, or a (meth)acryloxy radical, or is a hydrogen radical, preferably a methyl radical or hydrogen radical.

It is preferred here for the EO in the block to be terminal, it also being possible for the PO block to be terminal.

The tank mixture additive according to the invention is suitable in tank mixtures with crop protection compositions for all plants, although it stands out in particular in its effectiveness when used on grasses.

The tank mixture additive is advantageously used together with herbicides, fungicides, micronutrients or insecticides.

The compositions according to the invention comprising compounds according to Formula 1 are further particularly characterized in that they do not cause foam when used as tank mixture additive in spray mixtures.

Furthermore, the compositions according to the invention comprising compounds according to Formula 1 do not form micelles when used as 0.01 to 0.5% strength by weight aqueous solution, equivalent to 50 to 500 ml/ha in the spray mixture.

The invention further provides compositions comprising compounds of Formula 1 and polysiloxanes of general Formula 2

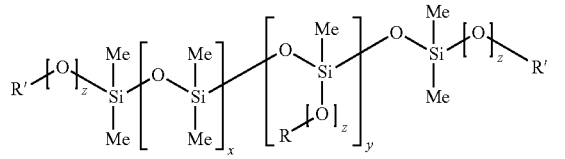

(Formula 2)

where
z=0 or 1,
x=0 to 100,
y=particularly greater than or equal to 0,
R'=R or an alkyl radical having 1 to 8 carbon atoms or a hydrogen atom,
R=$C_nH_{2n}O(C_eH_{2e}O)_pK$,
n=3 to 4,
e=identical or different 2 to 4,
p=greater than or equal to 3,
K=H, an alkyl radical having 4 or fewer carbon atoms.

The polysiloxanes of Formula 2 include in particular also hydrophilic polysiloxanes.

In these mixtures the mass mixing ratio of the components is 90:10 to 10:90 (Formula 1: Formula 2), but preferably 50:50 to 80:20. The mixtures should have a viscosity of max. 1000 mPas.

The compositions consisting of mixtures of compounds of Formula 1 and of Formula 2 as tank mixture additives can be used particularly advantageously for application with herbicides, fungicides or insecticides on grasses or cereals.

The compositions according to the invention can also particularly advantageously be used together with micronutrients, such as, for example, iron fertilizers, nitrogen fertilizers, trace element nutrients based on Cu, Fe, Zn, Mn, which are present, for example, as oxides, sulphates or carbonates.

Further subject matters of the invention arise from the claims, which are as a whole part of the disclosure of this description.

The formulations according to the invention and the process for their preparation are described by way of example below without the invention being able to be regarded as restricted to these exemplary embodiments. Where ranges, general formulae or compound classes are stated below, these are intended to include not only the corresponding ranges or groups of compounds which are explicitly mentioned, but also all part ranges and part groups of compounds which can be obtained by removing individual values (ranges) or compounds.

EXPERIMENTAL SECTION

The present invention is described by way of example in the examples listed below without the invention, the scope of application of which arises from the entire description and the claims, being deemed as restricted to the embodiments specified in the examples.

For the parent structures, the foam behaviour in aqueous solutions, the static and dynamic surface tension in 0.1% strength by weight aqueous solutions and the critical micelle concentration were measured according to CIPAC (Collaborative International Pesticides Analytical Council) method MT 47. The surface tension of 0.1% strength by weight solutions was measured using a bubble pressure tensiometer from SITA Messtechnik GmbH, instrument Sita online t 60; SITA online version 2.0. Bubble residence time of the dynamic surface tension is found at 5000 ms, of the static, at 30 ms. The measurement deviation is ca. 0.4 to 1% of the stated mN/m values. The measurements were carried out at an ambient temperature of 21.6° C. The values shown are average values from 5 measurements.

According to the definition of CIPAC, "non-foaming" products are those which only produce a foam of 5 ml in the measuring cylinder in the stated method and "foaming" applies to those which exhibit values of >20 ml. A tensid is a super spreader if by adding a small amount (0.1 weight percent) of this substance to a aqueous mixture, the aqueous mixture shows spreading into a thin layer on a hydrophobic surface within some (dozen) seconds—S. Zhu et al, Colloids and Surfaces A 1994, Vol. 90, pp. 63-78. Within this definition (super) spreading will occur if a droplet of approx. 0.05 mL spreads on the surface to a layer of more than 15-20 mm within 10 seconds.

At low surfactant concentrations, adsorption layers are formed on the water surface. Consequently, as the concentration of the surfactant increases, the surface tension decreases until the surfactant molecules are tightly packed in the adsorption layer. If the adsorption layer is saturated with unimers, the surface tension cannot drop further. The associated concentration is identical to the critical micelle concentration (cmc), thus to the concentration which is found at the break-point of a surface tension function. Above this concentration, micellar aggregates are formed in the volume phase from unimers.

A low surface tension is obtained if many unimers reach the newly derived surface within a short time. Substances which have a low cmc, so which form micelles, do not have a high free concentration of moving unimers and are therefore with a factor of 50-100 slower than substances with a large amount of unimers. Whereas substances with a high (or no) cmc have a large number of unimers with a high mobility, so they can fastly reach the surface and therewith decrease the surface tension. (J. K. Ferri, K. J. Stebe, A structure property study of the dynamic surface tension of three acetylenic diol surfactants, Colloids and Surfaces Part A, 156 (1999) p. 567-577 and J. K. Ferri, K. J. Stebe: "Which surfactants reduce surface tension faster? A scaling argument for diffusion controlled adsorbtion", Advances in Colloid and Interface Science 2000, 85, 61-97 see specifically page 85).

The function represents the dependency of the surface tension on the concentration of the surfactant solution. The measurements of the static surface tensions in the present surfactant solutions in dist. water were measured using the method of the hanging drop on account of the high precision required.

The resulting cmc values are listed in Table 1. Normally, cmc values are determined using the Wilhelmy plate method EN 14370. For this determination method, the liquid to be analysed must completely wet the plate. The disadvantage is that specifically wetting agents with hydrophobic moieties are also adsorbed on the plate and thus hydrophobicize the plate, i.e. incorrect surface tension values (in most cases too low) are determined.

The values forming the basis of this invention were determined by means of the method of the hanging drop, a fresh surface always being produced for determining the surface tension. This phenomenon can therefore not arise. The instrument used was an OCA 30 by DataPhysics (DataPhysics Instruments GmbH, Filderstadt, Germany) with six zoom lenses. The analysis instrument was equipped with a high-speed video system with CCD camera and a resolution of 768×576 at 132 Mbytes/s. The measurement accuracy stated by DataPhysics is 0.05 mN/m.

Besides measuring the surface tension, the ability of the additives or of the new additive mixtures to spread a water drop of volume 50 µl on a polypropylene surface was measured. The procedure for this spreading test is described by Venzmer et al. (J. Venzmer and S. P. Wilkowski: Trisiloxane Surfactants—Mechanisms of Wetting and Spreading, in: J. D. Nalewaja, G. R. Gross and R. S. Tann (eds.): Pesticide Formulations and Application Systems, Volume 18, ASTM Spec. Tech. Publ. 1347, American Society for Testing and Materials, 1998, 140-151); the spreading shows how much the target surface area can be covered by a 50 µl drop which contains the additive in a concentration of 0.1% by weight.

TABLE 1

Physical characterization of alkoxylated alcohols according to Formula 1 and their mixture with polysiloxanes of Formula 2 compared to the trisiloxane BREAK-THRU ® S240

|  | Comp. experiment 1 BREAK-THRU ® S240 | Structure according to Formula 1 | Formula 2 | Mixture of Formula 1 and 2 (70:30) |
|---|---|---|---|---|
| Static surface tension (mN/m) 0.1% by weight | 21.1 | 27 | 43.9 | 30 |
| Dynamic surface tension (mN/m) 0.1% by weight | 68 | 35.1 | 50.7 | 41 |
| Foam (ml) | 220 | 5 | 5 | 5 |
| Spreading (mm) | 70 | 15 | 5 | 14 |
| cmc(critical micelle concentration) | 0.01% by wt. | >0.5% by wt. | — | >1% by wt. |

As tank mixture additives here, a product according to Formula 1, where 3,5,5-trimethylhexanol was used as starting alcohol, and a mixture of 70 parts of Formula 1 and 30 parts of a compound according to Formula 2, where the compound according to Formula 2 is a hydrophilic polysiloxane, were compared to the commercial tank mixture additive BREAK-THRU® 5240.

It can be seen from Table 1 that at application concentrations at which tank mixture additives are used, namely 0.01 to 0.3% by weight, structures according to Formula 1 form no micelles compared to trisiloxanes (see in BREAK-THRU® S240) and therefore also demonstrate a very low dynamic surface tension.

Alkoxylated structures according to Formula 1 started with tertiary alcohols, or else mixtures with structures of Formula 2 are likewise non-foaming.

Thus, the compound of Formula 1 according to the invention surprisingly only exhibits the formation of micelle-like structures at a concentration of greater than or equal to 0.5% by weight, a concentration which is outside the normal application concentration of trisiloxane tank mixture additives.

The invention is further described by the following non-limiting examples which further illustrate the invention, and are not intended, nor should they be interpreted to, limit the scope of the invention.

Example 1

Field trial—increase in effectiveness of a herbicide against grasses by the structure according to the invention compared to the trisiloxane BREAK-THRU® 5240:

In a field trial with winter wheat, plots of 15 m$^2$ were divided randomly into 4 times repeated blocks. The four plots were sprayed in growth stage 24 (BBCH scale) of the winter wheat with the herbicide Ralon Super (EW 63 g/l of Fenoxaprop P, Nufarm Deutschland GmbH) and the wetting agents given in Table 2. Untreated plots were likewise prepared. At the time of spraying, the undesired harmful weed grass *Alepecurus myosuroides* (black grass) was dominant in the population. The products were diluted with water and applied at a water rate of 200 l/ha using a nozzle at a pressure of 1.5 bar.

The herbicide Ralon Super, which is known to only control monocotyledonous undesired grasses, but not harm the wheat, was applied at an application rate of 0.8 l/ha with and without the commercially available wetting agent BREAK-THRU® S240 (organomodified trisiloxane from Evonik Goldschmidt GmbH) and also the substance according to the invention, in each case in an amount of 0.15 l/ha. The degree of weed grass control was determined for 35 days following treatment in the manner known to the person skilled in the art by comparing the weed grass biomass in the treated plots to the weed biomass in untreated plots, and in so doing estimating the degree of effectiveness in percent. The effectiveness, averaged over four repetitions, of the weed grass control is given in Table 2.

The effectiveness data with different letters a and b differ in a statistically significant manner where P=0.05%; those values with the same letter are not statistically different. The results show that compound of the general Formula 1 according to the invention significantly improved the effectiveness of herbicides even compared with the commercial standard BREAK-THRU® S240.

TABLE 2

|  | Treatment | Effectiveness | Significance[1] |
|---|---|---|---|
| Cf. | Ralon Super | 89.0% | b |
| Ex. | Ralon Super + 0.15 l/ha of BREAK-THRU ® S240 | 91.3% | b |
| Ex. | Ralon Super + 0.15 l/ha of compound of Formula 1 (started with 3,5,5 trimethylhexanol) | 96.0% | a |

[1]Values with the same letter are statistically not significantly different (P = 0.05; calculated with Student-Newman-Keuls test using the ARM7 Software from Gylling Data Management (www.GDMDATA.com)).

It can be concluded from the trial that the example according to the invention promotes the control of weed grasses whereas this was the case only to a lesser degree in the case of the commercial standard Ralon Super.

Example 2

Greenhouse trial: influence of different adjuvants on the leaf attack of barley (variety "Hansa") with *Blumeria graminis* f. sp. *hordei* compared to the effect of the commercial product Amistar (azoxystrobin) upon protective application.

As tank mixture additives here, a product according to Formula 1, a mixture of compounds of the structure according to Formula 1 and 2, the compound according to Formula 2 being a hydrophilic polysiloxane, with a mixing ratio of 70:30% by weight, were compared to the commercial tank mixture additive BREAK-THRU® S240.

Trial Set-Up:

Barley plants (3 plants/vessel) were cultivated for three weeks in Frustorf earth. The fungicide AMISTAR (Syngenta; active ingredient azoxystrobin) was diluted alone or in a mixture with additives with water; 200 l/ha of spray mixture with the product amounts stated below were sprayed onto the plants using a nozzle. 6 hours following application of the entire plants with the test products, leaf segments 7 cm in length, starting from the base of the stem, were cut off and every 5 leaves of the youngest and second-youngest leaf were laid out on benzimidazole agar (0.5% agar, admixture of 40 ppm of benzimidazole following autoclaving). Inoculation of the leaves was carried out with fresh conidia of *Blumeria graminis* f. sp. *hordei* (strain A6) in the mildew tower by wind distribution. Afterwards, the leaves were incubated at room temperature. The amount of the preparations for the leaf application on whole plants was adjusted to 5 ml/ha. The water application rate was 250 l/ha, the application rate of the adjuvants was 25 ml/ha. (The active ingredient was thus 5 g/ha).

After incubation for 10 and 20 days at room temperature, the diseasing of the leaves with mildew was analysed by estimating the proportion of infected leaf area. This trial arrangement is familiar to the person skilled in the art.

Result: after 10 days, Amistar revealed as solo product, with 35% infestation, a moderate effect against mildew (the untreated control had 93% diseased leaf area). The degree of infestation upon adding the tank mixture additives to the Amistar spray mixture was on average as follows:

| | |
|---|---|
| Mixed product from Formula 1 and 2 | 1% |
| Formula 1 product | 1% |
| BREAK-THRU ® S240 | 5% |

All of the tested preparations containing products of Formula 1 exhibited an effect improvement of Amistar. 20 days following application, the effect of Amistar as solo product had further subsided, as the infestation degree of 51% documents. Under these conditions, however, in the case of the mixed product from Formula 1 and 2 and also in the case of the product according to Formula 1 and the BREAK-THRU® 5240, a noteworthy effect improvement of Amistar was still to be observed, as is evident from the infestation degrees:

| | |
|---|---|
| Mixed product from Formula 1 and 2 | 32% |
| Formula 1 product | 28% |
| BREAK-THRU ® S240 | 17% |

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method of reducing dynamic surface tension and/or foaming of a crop protection composition which comprises adding an alkoxylated alcohol of formula 1

$$R^1O(SO)_a(PO)_b(EO)_c(BO)_dR^2 \quad \text{(Formula 1)}$$

where

SO =styryloxy =—CH ($C_6H_5$) —$CH_2$—O— or —$CH_2$—CH($C_6H_5$) —O—,

PO =propyleneoxy =—CH ($CH_3$) —$CH_2$—O— or —$CH_2$—CH ($CH_3$) —O—,

EO =ethyleneoxy =—$CH_2$—$CH_2$—O—,

BO =butyleneoxy =—$CH_2$—$CH_2$—$CH_2$—$CH_2$—O—, a =0 to 1, b =0.5 to 4, c =1 to 5, d =0 to 1 and $R^1$ is a 3,5,5-trimethylhexyl radical, $R^2$ is an alkyl radical having 1 to 4 carbon atoms, an acyl radical, or a (meth)acryloxy radical, or is a hydrogen radical, as a tank mixture additive to the crop protection formulation.

2. The method of reducing dynamic surface tension according to claim 1, characterized in that $R^1$ in Formula 1 is a 3,5,5-trimethylhexyl radical and $R^2$ is a methyl radical or hydrogen radical.

3. The method of reducing dynamic surface tension of claim 1, wherein the composition further comprises one or more crop protection compositions in tank mixtures.

4. The method of reducing dynamic surface tension of claim 3, wherein the composition further comprises one or more crop protection compositions in tank mixtures for application to grasses and cereals.

5. The method of reducing dynamic surface tension of claim 1, wherein the composition further comprises herbicides, fungicides or insecticides.

* * * * *